(12) United States Patent
Burnier

(10) Patent No.: US 6,599,512 B1
(45) Date of Patent: Jul. 29, 2003

(54) ELECTROLYTE CONTENT W/O EMULSIONS FOR TREATING IRRITATED/ SENSITIVE SKINS

(75) Inventor: Véronique Burnier, Paris (FR)

(73) Assignee: La Roche Posay-Laboratoire Pharmaceutique, La Roche Posay (FR)

( * ) Notice: Subject to any disclaimer, the term of this patent is extended or adjusted under 35 U.S.C. 154(b) by 0 days.

(21) Appl. No.: 08/943,191

(22) Filed: Oct. 3, 1997

(30) Foreign Application Priority Data

Oct. 7, 1996 (FR) .............................. 96 12196

(51) Int. Cl.⁷ ................. A61K 9/107; A61K 33/14; A61K 33/24; A61K 47/34
(52) U.S. Cl. .................... 424/401; 424/400; 514/887; 514/937
(58) Field of Search ................. 424/401, 63, 400; 514/887, 937

(56) References Cited

U.S. PATENT DOCUMENTS

| | | | |
|---|---|---|---|
| 4,743,442 A | 5/1988 | Raaf et al. | 424/47 |
| 5,162,378 A | 11/1992 | Guthauser | 514/785 |
| 5,576,064 A | * 11/1996 | Fructus | 424/401 |

FOREIGN PATENT DOCUMENTS

| | | |
|---|---|---|
| EP | 0373661 | * 12/1989 |
| EP | 0373661 | 6/1990 |
| EP | 0435483 | * 12/1990 |
| EP | 0435483 | 7/1991 |
| EP | 0530531 | 3/1993 |

OTHER PUBLICATIONS

Chemical Abstracts, vol. 124, No. 8, Feb. 19, 1996, Columbus, Ohio, abstract No. 97268, & JP 07 277 922 A Oct. 24, 1995.

E.W. Flick: "cosmetic & toiletry formulations. Edition 2", 1989 Noyes Publication, p. 195.

E.W. Flick: "cosmetic and toiletry formulations", 1989, Noyes Publications, p. 751.

* cited by examiner

Primary Examiner—Edward J. Webman
(74) Attorney, Agent, or Firm—Burns, Doane, Swecker & Mathis, L.L.P.

(57) ABSTRACT

Stable, topically applicable water-in-oil emulsions, well suited for therapeutically treating irritated/sensitive skins and having high electrolyte content, comprise (a) at least 26 by weight of at least one water-soluble metal salt, (b) at least one hydrophobic gelling agent, (c) less than 5% by weight of at least one emulsifying agent, and, advantageously, at least one biologically active agent, for example an active agent that modulates skin differentiation and/or proliferation and/or pigmentation, an anti-inflammatory, an antibacterial, an antifungal, etc., and/or at least one keratolytic active agent, neuropeptide antagonist and/or inflammation-mediator antagonist.

32 Claims, No Drawings

ELECTROLYTE CONTENT W/O EMULSIONS FOR TREATING IRRITATED/SENSITIVE SKINS

BACKGROUND OF THE INVENTION

1. Technical Field of the Invention

The present invention relates to stable water-in-oil emulsions having a high electrolyte content, comprising at least 2% by weight, relative to the total weight of the composition, of a water-soluble metal salt, at least one hydrophobic gelling agent and an amount of a suitable emulsifying system effective to provide a stable composition, particularly a stable topically applicable composition.

This invention also relates to dermocosmetic compositions comprising the above stable w/o emulsions, for treating pathological and/or physiological disorders associated with the release of substance P and/or of TNF-alpha (Tumor Necrosis Factor-alpha) and, in particular, for treating sensitive skin and skin disorders and diseases in which pruritus, acne rosacea and/or discreet erythema exist.

2. Description of the Prior Art

It is known to this art that certain skin types are more sensitive than others. The symptoms of sensitive skin were hitherto poorly characterized and the problem of these skin types was consequently poorly defined since it was unknown exactly what process was involved in skin sensitivity/nonallergic hyperreactivity of the skin. Certain researchers considered that sensitive skin was a skin which reacted to cosmetic and/or dermatological products, while others considered that it was a skin which reacted to various external factors, not necessarily associated with cosmetic and/or dermatological products.

Certain tests have been conducted in an effort to characterize sensitive skin, for example tests using lactic acid and DMSO which are known irritants: see, for example, the article by K. Lammintausta et al., *Dermatoses*, 36, pages 45–49 (1988); and the article by XT. Agner and J. Serup, *Clinical and Experimental Dermatology*, 14, pages 214–217 (1989). However, these tests did not permit the characterization of sensitive skin, which was likened to allergic skin.

The symptoms associated with sensitive skin were demonstrated and described in FR-95/04,268 filed Apr. 10, 1995 and assigned to the assignee hereof. These symptoms are, in particular, subjective signs, which are essentially dysaesthetic sensations. By the term "dysaesthetic sensations" are intended the more or less painful sensations experienced in a region of skin, such as stinging, tingling, itching or pruritus, burning, heating, discomfort, tautness, etc.

It has also been shown that a sensitive skin was not an allergic skin, since an allergic skin is a skin which reacts to an external agent, an allergen, which triggers an allergic reaction. This is an immunological process which occurs only when an allergen is present and which affects only sensitized individuals. In contrast, the essential characteristic of sensitive skin is a mechanism of response to external factors, which may affect any individual, although individuals with so-called sensitive skin react faster thereto than others. This mechanism is not immunological, but a specific.

Sensitive skin may be divided into two major clinical categories, irritable skin and intolerant skin. An irritable skin is a skin which reacts, via pruritus, namely, by itching or by stinging, to various factors such as the environment, emotions, foods, the wind, rubbing, shaving, hard water having a high calcium concentration, temperature variations or wool. In general, these signs are associated with a dry skin with or without dartres, or with a skin which displays an erythema. An intolerant skin is a skin which reacts, by sensations of heating, tautness, tingling and/or redness, to various factors such as the application of cosmetic or dermatological products or soap. In general, these signs are associated with an erythema and with a hyperseborrhoeic or acneic skin, or even a rosaceiform skin, with or without dartres.

In general, sensitive skin is defined by a specific reactivity of the skin. This hyperreactivity may, in particular, be induced by environmental, emotional and dietary factors or, alternatively, by the application of or contact with cosmetic or dermatological products. This hyperreactive state which defines sensitive skin distinguishes such skin from the ubiquitous reactivity occasioned by irritant agents which induce a skin irritation in almost all individuals.

This hyperreactive state is experienced and recognized by individuals suffering therefrom as a "sensitive skin."

"Sensitive" scalps have a more univocal clinical semiology: the sensations of pruritus and/or of stinging and/or of heating are essentially triggered by local factors such as rubbing, soap, surfactants, hard water having a high calcium concentration, shampoos or lotions. These sensations are also in certain instances triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions, and in the crook of the elbow) and the feet, sensitive skin is reflected in pruriginous sensations and/or dysaesthetic sensations (heating, stinging) associated, in particular, with sweat, rubbing, wool, surfactants, hard water having a high calcium concentration and/or temperature variations.

Pruritus is a common symptom of dermatitis, which often causes considerable inconvenience to the patient. When the pruritus is very severe, the inconvenience may be such that the patient cannot continue his or her usual activity. In addition, pruritus may be a source of complications: excoriations which may become overinfected, lichenification of the pruriginous regions, the consequence of which is to position the patient in a veritable vicious circle. Among the forms of dermatitis often associated with pruritus, exemplary are eczema, a topic dermatitis, contact dermatitis, flat lichens, prurigo, urticaria pruriginous toxidermias and certain clinical forms of psoriasis.

Pruritus is sometimes the predominant pathological skin sign, as in the case of aquagenic pruritus, pruritus of the scalp while dandruff is present (pityriasis capitis), pruritus of blood dialysis patients, renal insufficiency, AIDS sufferers and individuals suffering from biliary obstructions, or pruritus of the paraneoplastic manifestations of certain cancers.

Further, pruritus is a sign often encountered over the course of certain parasitic attacks on the skin, or generally. These may be, for example, scabies, filariasis, oxyuriasis or demodicidosis of the skin.

Since the characteristics of sensitive skin are poorly understood, it was hitherto very difficult to treat it, and it was treated indirectly, for example by limiting the use of products irritant in nature, such as surfactants, preservatives or fragrances, as well as certain active agents, in cosmetic or dermatological compositions.

To date, pruritus was treated using emollient preparations, local corticoids, PUVA therapy or antihistamines. Local corticoids are, admittedly, very effective for alleviating the symptoms, but their effect is, unfortunately, not immediate. Too, they often elicit very severe side effects such as atrophy, and expose the patient to risks of mycosal and/or bacterial infections. PUVA therapy is the local irradiation of the diseased skin with UVA radiation, after absorption of a photosensitizing species (psoralen). This technique presents the major drawback of photoaging which may result in skin cancers. Further, this treatment is not ambulatory, thus obliging patients to regularly visit a specialized center throughout the treatment period, which is very restrictive and limits their professional activity. Emollients elicit a very modest anti-pruriginous effect and are of poor efficacy when the pruritus is considerable. Moreover, antihistamines are not of constant efficacy and must be administered orally.

Thus, serious need continues to exist in this art for improved treatment of the above skin afflictions which does present the above drawbacks.

The use of at least one metal salt, in particular an alkaline earth metal salt, for treating pruritus or "sensitive skin" problems effectively while at the same time avoiding the drawbacks indicated above is described in FR-95/04,268, filed Apr. 10, 1995 and assigned to the assignee hereof.

Gelled compositions having a high electrolyte content are described in FR-96/00,742 and FR-96/03,094, filed Jan. 27, 1996 and Mar. 12, 1996, respectively, also assigned to the assignee hereof.

In the cosmetic or dermatological field, it is common to topically apply creams consisting of a W/O emulsion containing an aqueous phase dispersed in an oily phase. These emulsions often have stability problems, which makes them difficult to formulate. Thus, various means have been attempted to overcome this drawback. One such means entails greatly increasing the emulsifier content of these emulsions. However, it is known that emulsifiers used in large amounts can elicit irritant effects on certain skin types. Moreover, as above, the creams obtained are often compact and heavy. It will readily be appreciated that such compositions are not suitable for application to sensitive skin, given the difficulties indicated above.

Various W/O emulsion compositions having a high electrolyte content are known to this art. Thus, EP-530,531 (Benckiser) describes a cosmetic composition formulated as an O/W or W/O emulsion comprising an emulsifying system and at least 2% (preferably at least 5%) of a water-soluble salt of alkali metals or of alkaline earth metals. The salt is preferably a magnesium salt, which serves as a preservative. These emulsions can be formulated into cosmetic compositions devoid of preservatives. For the W/O emulsions, the emulsifying system includes 5% to 10% by weight of the combination of a glycerol ester and of a copolymer of polyether alkyl silicones and a fatty acid ester.

Similarly, U.S. Pat. No. 5,162,378. (Revlon) describes a W/O microemulsion including 8% to 20% of an alkali metal or alkaline earth metal salt, 20% to 40% of water and 8% to 20% of an emulsifying system consisting of cetyl dimethicone copolyol, optionally supplemented with hexyl laurate and polyglyceryl-4 isostearate. These compositions comprising a high emulsifier content and a limited amount of water are not suitable for application to sensitive skin either.

SUMMARY OF THE INVENTION

Accordingly, a major object, of the present invention is the provision of novel stable water-in-oil (W/O) emulsions having high electrolyte content, well suited for topical application, and particularly effective for treating "sensitive skin" afflictions, especially pruritis.

This invention also provides cosmetic/dermatological compositions formulated from the subject novel W/O emulsions.

Briefly, the present invention features novel, stable W/O emulsions having a high electrolyte content, comprising at least 2% by weight, preferably at least 3% by weight and more preferably at least 5% by weight, relative to the total weight of the composition, of at least one water-soluble metal salt, at least one hydrophobic gelling agent and less than 5% by weight, also relative to the total weight of the composition, of a suitable emulsifying system.

DETAILED DESCRIPTION OF BEST MODE AND SPECIFIC/PREFERRED EMBODIMENTS OF THE INVENTION

More particularly according to the present invention, by the term "metal salt" is intended a salt of a metal, namely, a simple compound capable of liberating simple metal cations (*Dictionnaire de la Chimie et de ses Applications*, Duval & Duval, 3rd edition, 1978, Technique et Documentation).

The water-soluble metal salts are more particularly selected from among the water-soluble salts of alkali metals, or alkaline earth metals, of transition metals and of metals from Groups 13 and 14 of the Periodic Table.

Exemplary water-soluble salts of alkali metals according to the invention include, in particular, the lithium, sodium and potassium salts.

Exemplary water-soluble salts of alkaline earth metals according to the invention include, in particular, the beryllium, magnesium, calcium, strontium and/or barium salts.

Exemplary water-soluble salts of transition metals according to the invention include, in particular, the lanthanide salts and the salts of metals of the fourth period of the Periodic Table of the Elements, such as the magnesium, cobalt and zinc salts.

And exemplary water-soluble salts of metals from groups 13 and 14 of the Periodic Table of the Elements according to the invention include the aluminum and tin salts.

By the term "lanthanide" is intended the elements of atomic number z ranging from 57 to 71, i.e., lanthanum, cerium, praseodymium, neodymium, promethium, samarium, europium, gadolinium, terbium, dysprosium, holmium, erbium, thulium, ytterbium and lutetium.

Preferably, the water-soluble metal salts of this invention are selected from among the lithium, strontium, barium, yttrium, neodymium, gadolinium, manganese and zinc salts, more preferably the strontium salts.

These salts may be, for example, carbonates, bicarbonates, sulfates, glycerophosphates, borates, chlorides, nitrates, acetates, hydroxides and persulfates, as well as salts of α-hydroxy acids or salts of fruit acids (citrate, tartrate, lactate, malate), or salts of amino acids (aspartate, arginate, glucocholate, fumarate), or salts of fatty acids (palmitate, oleate, caseinate, behenate).

Preferably, the salts are selected from among the nitrates and chlorides, in particular lithium, strontium, barium, yttrium, neodymium, gadolinium, manganese or zinc nitrate, lithium, strontium, barium, yttrium, neodymium, gadolinium, manganese and zinc chloride, and sulfates and acetates, such as calcium, strontium and magnesium sulfate and strontium and magnesium acetate.

Advantageously, the amount of water-soluble metal salts in the emulsions according to the invention ranges from 2% to 20% by weight relative to the total weight of the composition, preferably from 5% to 10% by weight.

By the expression "suitable emulsifying system" is intended any emulsifying agent or mixture of emulsifying agents capable of providing a stable W/O emulsion having a high electrolyte content when they are present in the composition in an amount of less than 5% by weight relative to the total weight of the composition.

According to this invention, the expression "stable W/O emulsion" preferably connotes an emulsion which remains stable for at least 1 month at 45° C.

Advantageously, the suitable emulsifying system comprises at least one glycerol ester and/or at least one silicone polymer, which are suitable for the preparation of w/o emulsions.

Preferably, the glycerol ester is a polyglycerol ester of a fatty acid, in particular a polyglycerol ester of (iso)stearic acid, such as polyglyceryl-n isostearates, wherein n is an integer ranging from 2 to 6, marketed under the trademark Isolan by Goldschmidt.

Advantageously, the silicone polymer suitable for the preparation of an W/O emulsion is a polysiloxane, preferably a copolymer of polysiloxane polyalkyl polyethers, such as those described in DE-3,622,571, EP-125,779, EP-310,903 and EP-537,003 or in U.S. Pat. Nos. 4,421,656, 4,218,250, 4,268,499, 4,311,695, 4,122,029, 4,268,499 and 5,008,103. These are, more particularly, copolymers such as cetyl dimethicone copolyol, marketed under the trademark Abil by Goldschmidt or lauryl methicone copolyol marketed under the trademark DC5200 by Dow Corning.

Preferably, the suitable emulsifying system comprises at least one silicone polymer, which is suitable for the preparation of W/O emulsions, either singly or in combination with at least one glycerol ester.

When used in combination, the glycerol ester/silicone weight ratio advantageously ranges from 1/1 to 1/10, more preferably about 1/5.

Preferably, the amount of suitable emulsifying system ranges from 2% to 4% by weight relative to the total weight of the composition.

In addition, the emulsions according to the invention comprise at least one hydrophobic gelling agent. Exemplary such hydrophobic gelling agents include the modified clays such as bentones, silica, in particular hydrophobic silica, such as silyl or dimethylsilyl silica ("silica silylate" or "silica dimethyl silylate") marketed under the trademarks Aerosil R 812, R 972 or R 974 by Degussa, glycol ester derivatives of fatty acids, such as acetylated glycol stearate, optionally associated with a glycerol mono-, di- or triester of a fatty acid, such as tristearine, in particular the acetylated glycol stearate/tristearine mixture marketed under the trademark Unitwix by Guardian. The gelling agent is preferably silyl or dimethylsilyl silica or Unitwix.

The amount of hydrophobic gelling agent advantageously ranges from 0.01% to 5% by weight relative to the total weight of the composition, preferably from 0.1% to 3% by weight.

The aqueous phase of the emulsions according to the invention may comprise water, purified water, a floral water such as cornflower water, or a natural mineral or spring water, and mixtures thereof. For example, the natural mineral or spring water may be selected from among eau de Vittel, the waters of the Vichy basin, eau d'Uriage, eau de la Roche Posay, eau de la Bourboule, eau d'Enghien-les-Bains, eau de Saint Gervais-les-Bains, eau de Néris-les-Bains, eau d'Allevard-les-Bains, eau de Digne, eau de Maizieres, eau de Neyrac-les-Bains, eau de Lons-le-Saunier, les Eaux Bonnes, eau de Rochefort, eau de Saint Christau, eau des Fumades, eau de Tercis-les-Bains, eau d'Avéne and eau d'Aix-les-Bains.

The aqueous phase preferably comprises a spring water which is known for its soothing, anti-irritant, anti-free-radical properties when applied to the skin, in particular eau de la Roche Posay. Such spring waters generally have a high electrolyte content, in particular comprising water-soluble salts of alkaline earth metals. Obviously, the amount of alkaline earth metals in the spring water will be taken into account in order to determine the total amount of alkaline earth metals in the emulsions according to the invention.

The aqueous phase is advantageously present in an amount ranging from 40% to 80% by weight relative to the total weight of the composition, preferably from 50% to 70% by weight.

The fatty phase of the emulsions according to the invention may comprise fatty substances conventionally employed in the intended field of application. Exemplary of these are the silicone fatty substances such as silicone oils, as well as non-silicone fatty substances such as plant oils, mineral oils, animal oils or synthetic oils.

Representative silicone fatty substances are:
(i) poly($C_1$–$C_{20}$)alkylsiloxanes and, in particular, those containing terminal trimethylsilyl groups, including the linear polydimethylsiloxanes (PDMS) and alkylmethylpolysiloxanes such as cetyl dimethicone (CTFA name),
(ii) volatile silicone oils such as:
 (a) cyclic volatile silicones having from 3 to 8 and preferably from 4 to 6 silicon atoms; these include, for example, cyclotetradimethylsiloxane, cyclopentadimethylsiloxane and cyclohexadimethylsiloxane,
 (b) linear volatile silicones having from 2 to 9 silicon atoms; these include, for example, hexamethyldisiloxane, hexyl heptamethyltrisiloxane and octyl heptamethyltrisiloxane.

Exemplary non-silicone fatty substances include the usual oils., such as liquid paraffin, liquid petroleum jelly, almond oil, perhydrosqualene, apricot oil, wheatgerm oil, sweet almond oil, beauty-leaf oil, palm oil, castor oil, avocado oil, jojoba oil, olive oil or cereal germ oil; esters of fatty acids or of fatty alcohols, such as octyl dodecyl myristate or $C_{12}$–$C_{15}$ alkyl benzoates, alcohols; acetylglycerides; octanoates, decanoates or ricinoleates of alcohols or of polyalcohols; fatty acid triglycerides; glycerides; hydrogenated polyisobutene, hydrogenated oils that are solid at 25° C.; lanolins; fatty esters that are solid at 25° C.

These fatty substances are variously selected by one skilled in this art in order to formulate a composition having the desired properties, for example in terms of consistency or texture.

Thus, the fatty phase of the emulsions according to the invention is advantageously present in an amount ranging from 10% to 40% by weight relative to the total weight of the composition and preferably from 20% to 35% by weight.

In addition, the emulsions according to the invention may comprise at least one stabilizer which is suitable for a W/O emulsion having a high electrolyte content. Such stabilizers are selected, in particular, from among the alkali metal salts, for example sodium chloride, waxes and mixtures thereof in all proportions.

Exemplary waxes which are suitable stabilizers according to the invention include animal waxes, plant waxes, mineral waxes and synthetic waxes such as microcrystalline waxes, paraffin, petrolatum, petroleum jelly, ozokerite, montan wax; beeswax, lanolin and derivatives thereof; candelilla wax, ouricurry wax, carnauba wax, Japan wax, cocoa butter, cork fiber wax or sugar cane wax; hydrogenated oils that are solid at 25° C., ozokerites, fatty esters and glycerides that are solid at 25° C.; polyethylene waxes and the waxes obtained by Fischer-Tropsch synthesis; silicone waxes. Microcrystalline wax is the preferred.

The amount of stabilizer advantageously ranges from 0% to 5% by weight relative to the total weight of the composition, preferably from 0% to 3% by weight.

The emulsions according to the invention are advantageously formulated as a cream, a milk, a lotion, etc.

In known manner, the emulsions of the invention may also contain additives and adjuvants that are common in the cosmetic and/or dermatological fields, such as preservatives, antioxidants, complexing agents, solvents, fragrances, fillers (for example a matt-effect agent), UV-screening agents, bactericides, odor absorbers, dyestuffs, colorants, etc. The amounts of these various additives and adjuvants are those that are conventional in the field under consideration and, for example, comprise from 0.01% to 5% by weight relative to the total weight of the composition. Depending on their nature, these additives and adjuvants may be incorporated into the fatty phase or into the aqueous phase.

The emulsions/compositions according to the invention may also comprise at least one active agent which normally promotes a skin irritation.

The emulsions/compositions according to the invention are also useful for reducing the irritant effect of at least one active irritant compound administered separately in a cosmetic or pharmaceutical composition, topically (cream, lotion, gel, etc.) or systemically (orally, rectally or parenterally). The compositions according to the invention may be topically applied to the skin at the same time that the irritant active agent is administered, or combined but spread out over time.

Proteins or protein hydrolysates, amino acids, polyols, urea, allantoin, sugars and sugar derivatives, water-soluble vitamins, starch and bacterial or plant extracts, in particular those of Aloe vera, are exemplary hydrophilic active agents.

Retinol (vitamin A) and derivatives thereof, tocopherol (vitamin E) and derivatives thereof, essential fatty acids, ceramides and essential oils are exemplary lipophilic active agents.

These active agents are particularly intended for preventing and/or treating skin conditions/afflictions. Exemplary of these active agents are:

(a) agents which modify the differentiation and/or proliferation and/or pigmentation of the skin, such as retinoic acid and isomers thereof, retinol and esters thereof, retinoids, in particular those described in FR-2,570,377, EP-199,636, EP-325,540 and EP-402,072, retinal, vitamin D and derivatives thereof, estrogens such as estradiol, kojic acid or hydroquinone;

(b) antibacterial agents such as clindamycin phosphate, erythromycin or antibiotics of the tetracycline class;

(c) antiparasitic agents, in particular metronidazole, crotamiton or pyrethroids;

(d) antifungal agents, in particular compounds belonging to the imidazole class, such as econazole, ketoconazole or miconazole or salts thereof, polyene compounds such as amphotericin B, compounds of the allylamine family, such as terbinafine, or alternatively octopirox;

(e) steroidal anti-inflammatory agents such as hydrocortisone, betamethasone valerate or clobetasol propionate, or non-steroidal antiinflammatory agents such as ibuprofen and salts thereof, diclofenac and salts thereof, acetylsalicylic acid, acetaminophen or glycyrrhetinic acid;

(f) anaesthetics such as lidocaine hydrochloride and derivatives thereof;

(g) antipruriginous agents such as thenaldine, trimeprazine or cyproheptadine;

(h) antiviral agents such as acyclovir;

(i) keratolytic agents such as alpha- and beta-hydroxycarboxylic or beta-ketocarboxylic acids, salts, amides or esters thereof and, more particularly, alpha-hydroxy acids such as glycolic acid, lactic acid, tartaric acid, malic acid, citric acid, mandelic acid and, in general, fruit acids, and beta-hydroxy acids such assalicylic acid and derivatives thereof, in particular alkyl derivatives, such as 5-n-octanoylsalicylic acid;

(j) anti-free radical agents such as alpha-tocopherol or esters thereof, superoxide dismutases, certain metal chelating agents or ascorbic acid and esters thereof;

(k) antiseborrhoeic agents such as progesterone;

(l) antidandruff agents such as octopirox or zinc pyrithione;

(m) antiacne agents such as retinoic acid or benzoyl peroxide;

(n) antimetabolites;

(o) agents for combating hair loss such as minoxidil;

(p) antiseptic agents.

The emulsions/compositions according to the invention may also comprise, as active agents therefor, at least one keratolytic agent and/or at least one neuropeptide antagonist and/or at least one inflammation-mediator antagonist, various water-soluble metal salts, in particular for treating sensitive skin.

The present invention thus also features stable W/O emulsions having a high electrolyte content, comprising at least 2% by weight, relative to the total weight of the composition, of at least one water-soluble metal salt as described above, at least one active compound selected from among keratolytic agents, sly neuropeptide antagonists and inflammation-mediator antagonists other than water-soluble metal salts, at all least one hydrophobic gelling agent as described above and a suitable emulsifying system, also as described above.

Exemplary keratolytic agents according to the invention include alpha- and beta-hydroxycarboxylic or beta-ketocarboxylic acids, salts, amides or esters thereof and more particularly alpha-hydroxy acids such as glycolic acid, lactic acid, tartaric acid, malic acid, citric acid, mandelic acid and, in general, fruit acids, and beta-hydroxy acids such as salicylic acid and derivatives thereof, in particular alkyl derivatives, such as 5-n-octanoylsalicylic acid. Advantageously, these keratolytic agents are present in the emulsions/compositions according to the invention in amounts of up to 10% by weight relative to the total weight of the composition, preferably from 0.1% to 5% by weight.

Exemplary neuropeptide antagonists include substance P antagonists and CGRP antagonists, and exemplary inflammation-mediator antagonists include antagonists of histamine, of interleukin 1 or of TNFα. These antagonists are advantageously present in a proportion of from 0.000001% to 10% by weight relative to the total weight of the composition and preferably from 0.0001% to 5%.

Advantageously, substance P, CGRP and/or interleukin 1 receptor antagonists are formulated into the subject emulsions/compositions.

Exemplary substance P antagonists according to the invention include species of organic or inorganic origin which inhibit the receptor binding of substance P or inhibit the synthesis and/or release of substance P by sensitive nerve fibers.

The substance P receptor antagonist may, in particular, be a peptide or a non-peptide derivative containing a hetero atom, and more precisely a compound containing a heterocycle or a hetero atom bonded directly or indirectly to a benzene ring.

For example, sendide and spantide II are exemplary substance P receptor antagonist peptides.

The peptides described in U.S. Pat. Nos. 4,472,305, 4,839,465, EP-A-101,929, EP-A-333,174, EP-A-336,230, EP-A-394,989, EP-A-44,332, EP-A-498,069, EP-A-515,681, EP-A-517,589, WO-A-92/22,569 and GB-A-2,216,529 are also representative peptides.

The non-peptide substance P receptor antagonists which are useful according to the invention include, in particular, heterocyclic, especially sulfur-containing, nitrogen-containing or oxygen-containing compounds or compounds comprising a nitrogen atom bonded directly or indirectly to a benzene ring.

Exemplary such heterocyclic compounds are those described in EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05,525, WO-A-90/05,729, WO-A-91/18,878, WO-A-91/18,899, WO-A-92/12,151, WO-A-92/15,585, WO-A-92/17,449, WO-A-92/20,676, WO-A-93/00,330, WO-A-93/00,331, WO-A-93/01,159, WO-A-93/01,169, WO-A-93/01,170, WO-A-93/06,099, WO-A-93/09,116 and WO-A-94/08,997. In particular, compounds comprising at least one nitrogen-containing heterocycle include a 2-tricyclyl-2-aminoethane derivative, a spirolactam derivative, a quinuclidine derivative, an azacyclic derivative, an aminopyrrolidine derivative, a piperidine derivative, an aminoazaheterocycle and an isoindole derivative.

Exemplary compounds containing a nitrogen atom bonded directly or indirectly to a benzene ring include those described in EP-A-522,808 and WO-A-93/01,165.

And exemplary CGRP antagonists according to the invention include any species or substrate of organic or inorganic origin that inhibits the receptor binding of CGRP or inhibits the synthesis and/or release of CGRP by sensitive nerve fibers.

For an active species to be recognized as a CGRP antagonist, it must, in particular, satisfy the following characteristic of exhibiting CGRP-antagonist pharmacological activity, namely, inducing a coherent pharmacological response, in particular, in one of the following tests:

(1) the antagonist substance should decrease the vasodilation induced by capsaicin and/or (2) the antagonist substance should inhibit the release of CGRP by sensitive nerve fibers and/or (3) the antagonist substance should reduce inhibition of the contraction of the smooth muscle of the different canal induced by CGRP.

In addition, the CGRP antagonist may have an affinity for CGRP receptors.

CGRP 8-37, an anti-CGRP antibody, is an exemplary CGRP receptor antagonist according to the invention.

When the emulsions/compositions according to the invention comprise an active irritant compound that elicits skin irritation, selected from among keratolytic agents, neuropeptide antagonists and inflammation-mediator antagonists, other than water-soluble metal salts, the amount of emulsifying system will be effective to produce a stable composition, consistent with the stability criteria described above. Again, the minimum amount of emulsifying system is advantageously employed that produces a stable composition. A "suitable amount of emulsifying system" is thus an amount which is necessary and sufficient to provide a stable composition for at least 1 month at 45° C. This amount is preferably less than 10% by weight relative to the total weight of the composition, more preferably less than 8% by weight.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

The following W/O cream was formulated:

| Ingredients | % |
| --- | --- |
| A: Fatty phase: | |
| Polyglyceryl-4 isostearate | 0.50 |
| Cetyl dimethicone copolyol | 2.50 |
| $C_{12}$–$C_{15}$ alkyl benzoate | 1.00 |
| Octyldodecanol | 9.00 |
| Aluminum starch octenyl succinate | 3.00 |
| Dicaprylyl ether | 3.00 |
| Aerosil R 812 | 1.00 |
| B: Aqueous phase: | |
| Sodium chloride | 0.50 |
| Spring water | 69.20 |
| Strontium chloride | 6.00 |
| Preservative | 0.30 |
| C: Auxiliary phase: | |
| Cyclomethicone | 5.00 |

This W/O cream was formulated according to the following procedure:

(1) phases A and B were heated to 75° C. separately and phase B was then poured gradually into phase A at 600 rev/min;

(2) the mixture was permitted to cool with stirring at 600 rev/min, to 40° C.;

(3) phase C was then added at 1,500 rev/min, after which the emulsion was stirred at 3,000 rev/min for 5 min.

An emulsion which was stable for at least 1 month at 45° C. was obtained.

EXAMPLE 2

The following W/O cream was formulated:

| Ingredients | % |
| --- | --- |
| A: Fatty phase: | |
| Polyglyceryl-4 isostearate | 0.50 |
| Cetyl dimethicone copolyol | 2.50 |
| $C_{12}$–$C_{15}$ alkyl benzoate | 3.00 |
| Capryloylsalicylic acid | 1.00 |
| Octyldodecanol | 11.00 |
| Aluminum starch octenyl succinate | 3.00 |

-continued

| Ingredients | % |
| --- | --- |
| Dicaprylyl ether | 3.00 |
| Acetylated and tristearine glyceryl stearate (UNITWIX) | 1.50 |
| B: Aqueous phase: | |
| Spring water | 62.00 |
| Strontium chloride | 6.60 |
| Preservative | 0.90 |
| C: Auxiliary phase: | |
| Cyclomethicone | 5.00 |

The emulsion was formulated according to the procedure of Example 1. A composition which was stable for at least 1 month at 45° C. was also obtained.

EXAMPLE 3

The following W/O cream was formulated:

| Ingredients | % |
| --- | --- |
| A: Fatty phase: | |
| Polyglyceryl-4 isostearate | 0.50 |
| Cetyl dimethicone copolyol | 2.50 |
| $C_{12}$–$C_{15}$ alkyl benzoate | 3.00 |
| Capryloylsalicylic acid | 1.00 |
| 2-Hexyldecanol, 2-octyldecanol, 2-hexyldodecanol and 2-octyldodecanol | 11.00 |
| Aluminum starch octenyl succinate | 3.00 |
| Dicaprylyl ether | 3.00 |
| Stabilizer | 3.00 |
| B: Aqueous phase: | |
| Spring water | 60.50 |
| Strontium chloride | 6.60 |
| Preserving agent | 0.90 |
| C: Auxiliary phase: | |
| Cyclomethicone | 5.00 |

The emulsion was formulated according to the procedure of Example 1. A composition which was stable for at least 1 month at 45° C. was also obtained.

The W/O emulsions according to the invention exhibited better tolerance for alkaline earth metal salts than the corresponding O/W emulsions, for individuals suffering from pruritus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable water-in-oil emulsion suited for topical application to irritated/sensitive skins and having a high electrolyte content, comprising (a) at least 2% by weight of at least one water-soluble metal salt, (b) at least one hydrophobic gelling agent which is selected from the group consisting of a modified clay, a hydrophobic silica and a glycol ester derivative of a fatty acid, and (c) less than 5% by weight of at least one emulsifying agent wherein said at least one emulsifying agent comprises at least one glycerol ester and at least one silicone polymer.

2. A stable water-in-oil emulsion suited for topical application to irritated/sensitive skins and having a high electrolyte content, comprising:

(a) at least one water-soluble metal salt, in an amount of at least 2% by weight;

(b) at least one hydrophobic gelling agent comprising at least one member selected from the group consisting of a modified clay, a hydrophobic silica and a glycol ester of a fatty acid, in an amount of from 0.01% to 5% by weight; and (c) at least one glycerol ester emulsifying agent and at least one silicone polymer emulsifying agent, in a combined amount effective to provide a stable emulsion, said amount being less than 5% by weight.

3. The water-in-oil emulsion as defined by claim 2, comprising at least 3% by weight of said at least one water-soluble metal salt (a).

4. The water-in-oil emulsion as defined by claim 3, comprising at least 5% by weight of said at least one water-soluble metal salt (a).

5. The water-in-oil emulsion as defined by claim 2, said at least one water-soluble metal salt (a) comprising a water-soluble salt of an alkali metal, of an alkaline earth metal, of a transition metal and/or of a metal from Groups 13 and 14 of the Periodic Table.

6. The water-in-oil emulsion as defined by claim 5, said at least one water-soluble metal salt (a) comprising a lithium, strontium, barium, yttrium, neodymium, gadolinium, manganese and/or zinc salt.

7. The water-in-oil emulsion as defined by claim 2, said at least one water-soluble metal salt (a) comprising a carbonate, bicarbonate, sulfate, glycerophosphate, borate, chloride, nitrate, acetate, hydroxide, persulfate, salt of an α-hydroxy acid, salt of an amino acid and/or a salt-of a fatty acid.

8. The water-in-oil emulsion as defined by claim 2, comprising from 2% and 20% by weight of said at least one water-soluble metal salt (a).

9. The water-in-oil emulsion as defined by claim 2, wherein said at least one glycerol ester emulsifying agent comprises a polyglycerol ester of a fatty acid.

10. The water-in-oil emulsion as defined by claim 2, wherein said at least one silicone polymer emulsifying agent comprises a polysiloxane.

11. The water-in-oil emulsion as defined by claim 10, wherein said polysiloxane comprises a copolymer of cetyl dimethicone and lauryl methicone copolyol.

12. The water-in-oil emulsion as defined by claim 2, wherein the glycerol ester emiulsifying agent/silicone polymer emulsifying agent weight ratio ranges from 1/1 to 1/10.

13. The water-in-oil emulsion as defined by claim 2, comprising from 2% to 4% by weight of said (c).

14. The water-in-oil emulsion as defined by claim 2, said at least one hydrophobic gelling agent (b) comprising admixture of acetylated glycol stearate and a glycerol triester of a fatty acid.

15. The water-in-oil emulsion as defined by claim 2, said at least one hydrophobic gelling agent (b) comprising a silyl or dimethylsilyl silica.

16. The water-in-oil emulsion as defined by claim 1, the aqueous phase of which comprising a purified water, a floral water, a natural mineral or spring water, or mixture thereof.

17. The water-in-oil emulsion as defined by claim 2, the aqueous phase of which comprising from 40% to 80% by weight thereof.

18. The water-in-oil emulsion as defined by claim 2, the fatty phase of which comprising from 10% to 40% by weight thereof.

19. The water-in-oil emulsion as defined by claim 6, said at least one water-soluble metal salt (a) comprising a strontium salt.

20. The water-in-oil emulsion as defined by claim 8, comprising from 5% to 10% by weight of said at least one water-soluble metal salt (a).

21. The water-in-oil emulsion as defined by claim 9, wherein said polyglycerol ester of a fatty acid comprises a polyglycerol ester of (iso)stearic acid.

22. The water-in-oil emulsion as defined by claim 10, wherein said polysiloxane comprises polysiloxane polyalkyl polyether copolymer.

23. The water-in-oil emulsion as defined by claim 2, further comprising at least one active agent which normally promotes skin irritation.

24. The water-in-oil emulsion as defined by claim 2, further comprising at least one biologically active agent.

25. The water-in-oil emulsion as defined by, claim 24, said at least one biologically active agent (c) comprising an agent for modulating skin differentiation and/or proliferation and/or pigmentation, an antibacterial agent, an antiparasitic agent, an antifungal agent, a steroidal anti-inflammatory agent or non-steroidal anti-inflammatory agent, an anaesthetic agent, an antipruritic agent, an antiviral agent, a keratolytic agent, an anti-free radical agent, an antiseborrhoeic agent, an antidandruff agent, an anti-acne agent, an antimetabolite, an agent for combating hair loss, an antiseptic or combination thereof.

26. The water-in-oil emulsion as defined by claim 2, further comprising at least one keratolytic active agent, and/or at least one neuropeptide antagonist and/or at least one inflammation-mediator antagonist, other than a water-soluble metal salt.

27. The water-in-oil emulsion as defined by claim 26, further comprising at least one alpha- or beta-hydroxycarboxylic or beta-ketocarboxylic acid, or salt, amide or ester thereof.

28. The water-in-oil emulsion as defined by claim 26, further comprising at least one substance P antagonist and/or at least one CGRP antagonist.

29. The water-in-oil emulsion as defined by claim 26, further comprising at least one antagonist of histamine, of interleukin 1, and/or of TNFα.

30. The water-in-oil emulsion as defined by claim 2, further comprising at least one salt or wax stabilizer therefor.

31. The water-in-oil emulsion as defined by claim 2, comprising a cream, milk, gel or lotion.

32. A dermocosmetic composition of matter comprising the water-in-oil emulsion as defined by claim 2.

* * * * *